United States Patent [19]

Liu

[11] Patent Number: 5,552,324
[45] Date of Patent: Sep. 3, 1996

[54] METHOD AND APPARATUS FOR DETERMINING THE CONCENTRATION OF READILY OXIDIZABLE ORGANIC VAPORS IN GAS SAMPLES

[75] Inventor: Francis P. Liu, State College, Pa.

[73] Assignee: Supelco, Inc., Bellefonte, Pa.

[21] Appl. No.: 193,249

[22] Filed: May 23, 1994

Related U.S. Application Data

[63] Continuation of Ser. No. 893,611, Jun. 5, 1992, abandoned.

[51] Int. Cl.$^6$ ........................................ G01N 1/22
[52] U.S. Cl. ..................... 436/132; 436/166; 436/900; 422/84
[58] Field of Search ..................... 436/32, 127, 132, 436/166, 900; 422/83–84

[56] References Cited

U.S. PATENT DOCUMENTS

| | | | |
|---|---|---|---|
| 2,591,691 | 4/1952 | Forrester et al. | 23/232 |
| 2,939,768 | 6/1960 | Grosskopf | 23/232 |
| 3,223,488 | 12/1965 | Luckey | 23/254 |
| 3,455,654 | 7/1969 | McConnaughey | 23/232 |
| 3,582,274 | 6/1971 | Keyes et al. | 23/232 |
| 3,684,456 | 8/1972 | McConnaughey | 23/254 R |
| 3,725,007 | 4/1973 | Kral et al. | 23/254 R |
| 4,155,358 | 5/1979 | McAllister et al. | 436/126 |
| 4,656,008 | 4/1987 | Gump | 422/86 |
| 4,740,475 | 4/1988 | Paul | 436/167 |
| 4,791,065 | 12/1988 | Rislova | 436/132 |

OTHER PUBLICATIONS

Shriner et al., "The Systematic Identification of Organic Compounds", pp. 192–195, John Wiley & Sons, (1980).

Regan et al., J. American Chem. Soc. 99:11, pp. 3837–3838, (1977).

Peters et al., "Chemical Separations and Measurements", pp.100–104, and 310, (1974).

Peters et al., "A Brief Introduction to Modern Chemical Analysis", pp.217–221,(1976).

Hawley, "The Condensed Chemical Dictionary", 10th Edition, p.155, Van Nostrand Reinhold Company, Inc., (1981).

*Primary Examiner*—Lyle A. Alexander
*Attorney, Agent, or Firm*—Senniger, Powers, Leavitt & Roedel

[57] ABSTRACT

A reagent, an apparatus and a method for semi-quantitatively estimating the concentration of readily oxidizable organic vapors in a gas sample, as for example ethanol in a human breath sample, is disclosed. The ethanol-sensitive solid indicator is a solid support which contains a permanganate salt and is wetted by a strongly acidic or alkaline solution. In the presence of ethanol the indicator produces a clearly visible color change. The apparatus contains the indicator and provides a pathway for a gas sample through the indicator. The method allows estimation of the organic-vapor content of a gas sample by comparing the volume of indicator which changes color in response to the gas sample with the volume which changes color in response to a known-concentration standard.

29 Claims, 1 Drawing Sheet

METHOD AND APPARATUS FOR DETERMINING THE CONCENTRATION OF READILY OXIDIZABLE ORGANIC VAPORS IN GAS SAMPLES

This is a continuation of application Ser. No. 07/893,611, filed Jun. 5, 1992 now abandoned.

FIELD OF THE INVENTION

This invention relates to a method and device for semi-quantitative determination of ethanol in mammalian breath samples, and more particularly to a breath-analyzing method and device which employ a solid support impregnated with a permanganate to indicate colorimetrically the presence and amount of ethanol in a gas sample.

BACKGROUND OF THE INVENTION

Blood alcohol content relates directly to the alcohol concentration in alveolar breath. This relationship allows a non-invasive estimation of blood alcohol levels by measuring breath alcohol levels. Simple devices that may be used for field determination of alcohol content in exhaled breath are of increasing interest, not only for police and others charged with regulating highway safety, but for those serving alcoholic beverages, as recent court cases have held such persons responsible for damage done by their intoxicated patrons or guests. A variety of devices for determining alcohol levels of human subjects are known, as for example that shown by Forrester in U.S. Pat. No 2,591,691, which describes a device that permits exhaled breath to be forced through an acidic solution of potassium permanganate at a flow rate of at least 800 ml per minute. By measuring the time required to decolorize the solution, the breath alcohol content, and from that the degree of intoxication, may be estimated. The device is simple and the test is fast, but the color change from pink to colorless is not distinct. The colored oxidizing solution also must be prepared immediately prior to testing, by mixing specific amounts of a standard potassium permanganate solution and a known-concentration sulfuric acid solution, as the solution will deteriorate rapidly on standing.

Permanganate salts coated on solid supports such as molecular sieve, silica gel and clay have been reported by Regen et al., in J. Am. Chem. Soc. 99, pp. 3837–3838 (1977) for oxidation of alcohol in organic solvents at 70° C. under neutral conditions, but not as a colorimetric reagent.

Other devices for semi-quantitative determination of alcohol in breath use the color change produced when ethanol is oxidized by chromate anion under strongly acidic conditions. For example, Grosskopf, in U.S. Pat. No. 2,939,768, discloses a reagent made by impregnating silica gel with potassium dichromate, sulfuric acid, arsenic trioxide and iodine. A simpler version, in which the arsenic trioxide and iodine have been removed, is disclosed by Luckey in U.S. Pat. No. 3,223,488. Other variations have been disclosed. A similar reagent, in which the sulfuric acid has been replaced by metaphosphoric acid, is shown by McConnaughey in U.S. Pat. No. 3,455,654, and the sulfuric acid may be augmented with a pentavalent phosphorous compound and perchloric acid, as shown by McConnaghey in U.S. Pat. No. 3,684,456. Keyes, in U.S. Pat. No. 3,582,274, shows another version which uses a nitric acid solution as the acid source.

Devices based on these reagents have been disclosed as well, as for example the tube of Kral et al., U.S. Pat. No. 3,725,007, which contains glass particles bonded with silica gel that is impregnated with dichromate and sulfuric acid, and the combination of a tube containing acid and dichromate protected by silica-gel desiccant, shown by Gump in U.S. Pat. No. 4,656,008. Rislove discloses, in U.S. Pat. No. 4,791,065, silica gel as a solid carrier for the acid and dichromate.

The color change of the dichromate-acid reagent in the presence of ethanol is relatively distinct and may be from an initial orange or yellow color to an exposed green or dark green color, depending on the manufacturers' methods. The change is slow, however, and the reagents are corrosive and toxic. Chromate is a carcinogen, and both the chromate and the acid are environmental hazards, which complicates disposal.

Thus a need exists for a device and method which permits rapid and reliable estimation of ethanol in breath samples, is safe and easy to manufacture, is stable for storage and easily used in the field, and does not create disposal problems.

SUMMARY OF THE INVENTION

I have discovered a colorimetric reagent, a device and a method which permit rapid, semi-quantitative estimation of readily oxidizable organic vapors in gas samples, and particularly of ethanol in breath samples; these are described in detail below.

The colorimetric reagent of the present invention comprises an inert, porous, solid support impregnated with a water-soluble permanganate salt and wetted with an aqueous acidic or basic solution which, on exposure to readily oxidizable organic vapors in a gas sample, as for example, ethanol in breath, undergoes a readily perceptible color change. In another embodiment, a precursor to this colorimetric reagent comprises an inert, porous, solid support impregnated with a water-soluble permanganate salt, and separated therefrom, an acidic or basic solution, the support and solution being stable in storage while separated, but being readily combinable to form the colorimetric reagent.

In a simple aspect, the apparatus of the present invention comprises a transparent or translucent vessel having an inlet opening and an outlet opening, and disposed within the vessel an inert, porous, solid, support impregnated with a permanganate salt. In a preferred embodiment the vessel is cylindrical in shape, with the inlet and outlet openings disposed at either end of the cylinder, and the inlet opening is sized such that it may readily be sealed by the lips of an adult human being, so that breath may be forced into the inlet opening, through the solid support and out the exit opening.

In another aspect, the apparatus of the present invention comprises a transparent or translucent vessel having an inlet opening and an outlet opening, and contained within the vessel (a) an inert, porous, solid support impregnated with a permanganate salt disposed nearer the outlet opening, and (b) an acidic or alkaline solution disposed nearer the inlet opening, the support and the solution being separated from contact with one another by a barrier disposed within the vessel, the barrier being sufficiently porous to allow the solution to be forced under pressure through the barrier to contact the support, but not sufficiently porous to allow the solution to flow through the barrier by capillary action or gravity.

In yet another aspect, the apparatus of the present invention comprises a flexible, non-frangible, translucent or transparent vessel having an inlet opening and an outlet opening, and contained within the vessel (a) a solid support impregnated with a permanganate salt and (b) an acidic or alkaline solution, the solution being prevented from contact with the support by a frangible barrier disposed within the vessel in such a manner as to be broken when the vessel is flexed, whereupon the solution may be forced under pressure into contact with the support.

The method of the present invention for detecting the presence of readily oxidizable organic vapor in a gas sample comprises contacting the gas sample with an inert, porous, solid support impregnated with a permanganate salt and activated by wetting with an alkaline or acidic solution, observing the volume of support in which a color change occurs, and estimating the amount of readily oxidizable organic vapors in the sample by comparison to the volume of activated, permanganate-impregnated support which changes color in response to a gas sample of the same volume containing a known concentration of readily oxidizable organic vapors. In a preferred embodiment of the method, the solution is separated from the support, and the method further comprises the step, carried out prior to contacting the support with the gas sample, of wetting the support with the solution.

In another preferred embodiment of the method, the support wetted with the solution is contained within a cylindrical vessel having an inlet opening and an outlet opening disposed at opposite ends of the vessel, a gas sample of known volume is forced under pressure into the vessel and through the support, and the concentration of readily oxidizable vapor in the gas sample is estimated from the fraction of the support which is observed to change color. In a more preferred embodiment of the method, the gas sample is the breath of a human test subject, the gas sample is forced under pressure into the vessel and through the support by the test subject blowing into the inlet opening a measured volume of breath, and the concentration of ethanol in the breath is estimated from the fraction of support which is observed to change color.

DETAILED DESCRIPTION OF THE INVENTION

Figure 1:
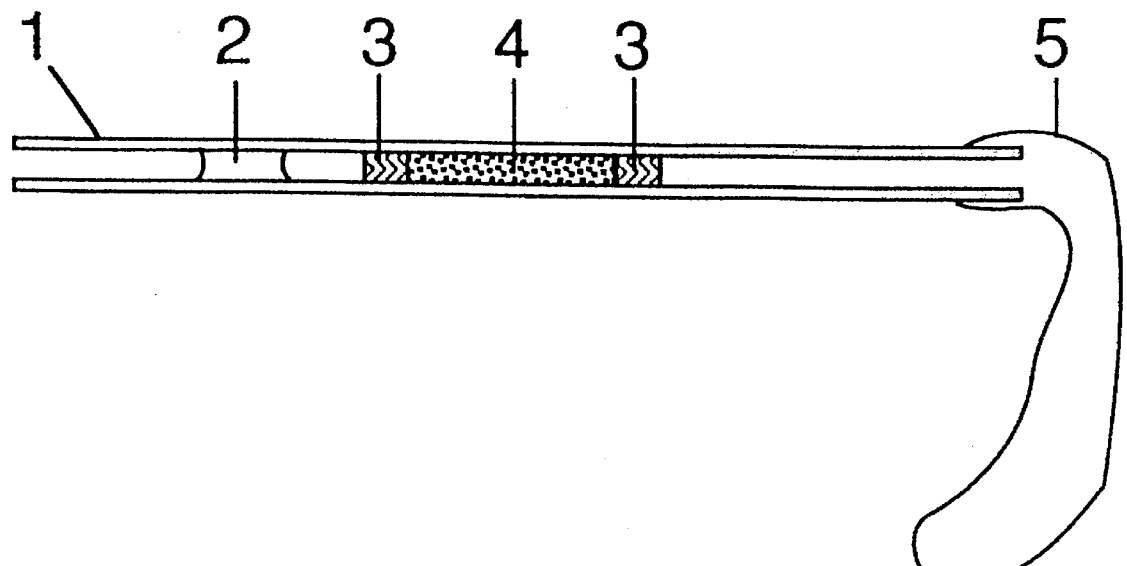
FIG. 1 shows one embodiment of the device of the present invention for estimating readily oxidizable organic vapors in gas samples; this particular embodiment is especially well suited to estimation of ethanol in breath samples. The permanganate-impregnated support of the present invention (4) is disposed within the vessel, in this case a cylindrical tube (1), and is held in place with plugs of glass wool (3). The activating reagent (2) is disposed within the tube where breath passing through the tube will force it into contact with the permanganate-impregnated support. The breath is collected in a flexible but inelastic gas-sampling vessel (5) that permits breath to flow through the activated support up to the known volume of the gas-sampling vessel.

The method of the present invention is based upon the oxidation of a readily oxidizable organic vapor by permanganate in the presence of a strongly acidic or alkaline catalyst. Under alkaline conditions, the oxidation proceeds initially with the rapid reduction of the red permanganate to the green manganate, according to the following reaction:

The manganate is more slowly reduced to the brown manganese dioxide according to the following reaction:

These reactions produce an easily visible color change in the support as readily oxidizable organic vapor contacts the permanganate, from a light pink to green until the permanganate is converted to manganate, and then to brown as the manganate is converted to manganese dioxide in the presence of additional, readily oxidizable organic vapor.

Under acidic conditions the permanganate is reduced directly to the colorless manganous ion by the following reaction:

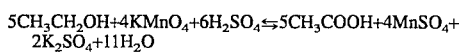

The preferred reaction is that under alkaline conditions, as the disappearance of the pink color in response to contact with the readily oxidizable organic vapor under acidic conditions is slower and somewhat less distinct than the change to green and then brown under alkaline conditions.

The permanganate readily reacts with such readily oxidizable organic materials as alcohols, ketones, aldehydes, amines, and the unsaturated bonds of alkenes and alkynes. Because the reaction is with these groups themselves, the remainder of the molecule to which these groups are attached is relatively unimportant, so long as that molecule does not deactivate the group to the extent that it is no longer readily oxidizable. Lower alkyl molecules, as for example, $C_1$ through $C_8$ alkyl molecules, containing the above groups are more likely to be encountered in gas samples, and are thus the preferred organic vapors to be detected, but other readily oxidizable organic vapors may also be detected. For instance, contemplated within the scope of the present invention is an air quality monitor for estimating concentrations of readily oxidizable organic vapors in air, in which air samples are pumped under pressure, or drawn under vacuum, through the colorimetric reagent to produce the observable color change in the reagent. Other variations within the scope of the present invention will readily be apparent to those skilled in the art.

A particularly preferred molecule to be detected by the present invention is ethanol, and especially ethanol in the breath (alveolar ethanol) of human test subjects. As noted in the "Background of the Invention" section, the concentration of alveolar ethanol relates to the concentration of alcohol in the blood, and blood-alcohol concentration relates to the degree of alcohol intoxication of the human test subject. Those skilled in the art will recognize that the present method is sensitive to readily oxidizable organic vapors other than ethanol which may be present in the breath of certain test subjects, for example, those suffering from certain metabolic diseases and from intoxication by other organic materials. For this reason the results obtained by using the method of the present invention should not be interpreted as necessarily indicating a particular level of ethanol intoxication in a test subject, but rather as a guide in situations where ethanol intoxication is suspected because of other information.

Of particular advantage is the ease of using the method and device of the present invention, the rapidity with which a result is obtained, the ease of observing the color change, the relative ease and safety of manufacturing the colorimetric reagent, and the relatively innocuous nature of the used materials for waste disposal, especially when the method is compared with colorimetric methods using dichromate indicators.

The reagents of this invention are easily prepared by treating a solid support with a solution of a permanganate salt. Suitable porous, solid supports include materials which can be impregnated with permanganate without rapid decomposition of the permanganate or support and will allow passage of a gas stream. The preferred supports are particulate, and have a preferred mean particle size of from about 100 µm to about 1 mm, and a more preferred mean particle size of from about 250 µm to about 850 µm. Smaller particle sizes may be used, but the pressure drop across a mass of the particles increases rapidly with decreasing particle size, and particularly in the case of a human test subject who must force breath through the mass of particles, the pressure required may be impractical. Larger particle sizes may also be used, but excessive gas flow may occur within the interstices among the particles, providing inadequate contact of the gas with the permanganate in the support. Useful supports include molecular sieves, silica, alumina, and magnesia. Molecular sieves are preferred.

The permanganate solution is prepared such that the concentration of permanganate on the support will show a distinct color change at the ethanol concentrations of interest. The solution may be prepared using a solvent for a permanganate salt; water is the preferred solvent, and water-soluble permanganate salts are preferred, as for example alkali metal permanganates salts such as lithium, sodium and potassium permanganate. More preferred is potassium permanganate. The solution may be prepared at concentrations up to saturation of the permanganate salt in the solvent, as for example up to about 6 g potassium permanganate in 100 ml water. The saturated solution tends to be more stable on storage than lower dilutions, and may readily be diluted for application to the support. A concentration which is high enough to impregnate the support in a single application with at least enough permanganate salt to produce an observable color change on activation and exposure to ethanol, without introducing so much water that the support no longer flows freely, is the minimum practical concentration for the solution.

The concentration of permanganate salt on the support must be at least high enough to produce an observable color change, and preferably high enough that the amount of readily oxidizable organic vapor in a gas sample would not reduce all the permanganate in the amount of impregnated support to which it is exposed. Although support impregnated with low levels of permanganate salt may be used in some applications of this method by increasing the amount of impregnated support exposed to the organic vapors, practical considerations such as an increase in the force with which a test subject must blow to force breath through a given diameter tube, or difficulty in wetting the support with the activating solution as tube diameter is increased, limit the amount of impregnated support for a practical breath-ethanol testing tube.

Levels ranging from about 14 milligrams (mg) of potassium permanganate per gram of support to about 0.7 mg of potassium permanganate per gram of support are preferred for most uses, and levels from about 7 mg to about 3 mg of potassium permanganate per gram of support are more preferred, especially for breath-ethanol testing. If other permanganate salts are used, the permanganate level should be adjusted based upon the ratio of the molecular weights of the particular salt and potassium permanganate.

The following is presented as a guide to one skilled in the art for the practice of the present invention. The alveolar breath of a standard human test subject having a blood alcohol content (BAC) of 0.10% is taken as 0.476 mg ethanol per liter of breath. From the equation for the reduction of potassium permanganate by ethanol to form potassium manganate, presented above, one may readily calculate that this amount of ethanol will reduce 6.54 mg of potassium permanganate to potassium manganate. In the examples below, the volume of the breath samples was approximately 210 ml, so the amount of potassium permanganate reduced by the breath sample of that size, taken from a standard human test subject having a BAC of 0.10%, will be approximately 1.37 mg. Clearly it is desirable to have the color change for that BAC occur in more than half the impregnated support in the tube, to offer the greatest sensitivity of the test in the range below levels generally accepted as "intoxication." Thus the impregnated support in the tube should contain approximately 2 mg potassium permanganate, which would require from about 2.9 g of support impregnated with 0.7 mg $KMnO_4$/g support to about 0.14 g of support impregnated with 14 mg $KMnO_4$/g support, the preferred range of concentrations set forth above. One of ordinary skill in the art may readily select an amount of support needed to create a support column in the vessel (e.g., tube) having sufficient length to facilitate estimation of the percentage of support that has changed color, and from the above determine the potassium permanganate concentration for the impregnated support required to have about 2 mg potassium permanganate present in the tube. One of ordinary skill in the art may then readily modify the above as needed, to compensate for different permanganate salts, different diameters and lengths of tubes, different target concentrations of ethanol, different breath-sample sizes, different organic vapors other than ethanol, and different gas sampling, as for example determining organic vapor in air by pumping air through the tube containing the activated, impregnated support.

The permanganate-impregnated support is prepared by contacting the support with the permanganate solution and allowing it to adsorb into the support. The volume of permanganate solution used to contact the support must be sufficient to homogeneously adsorb onto the solid support, but not so great as to cause lumping of the support. Particularly where the support is molecular sieves, the support will tend to form lumps rather than a free-flowing powder at water contents in the range of about 50 to 60%, based on the weight of dry support, so the water content of the impregnated support is preferably less than about 50%. Activated support which initially contained less than about 3% water prior to activation has been observed to change color more slowly than activated support containing more than about 5% water prior to activation, so a preferred amount of water in the impregnated support prior to activation is about 5% or more, based on the weight of the dry support. Molecular sieves tend to be highly hygroscopic, and if they are not specially treated to remove adsorbed water, may be expected to contain several percent water, typically about 6 to about 7% water, based an the weight of dry support. Adding water as part of the permanganate solution will increase the level of this water content in the support, so permanganate-impregnated, molecular-sieve support would be expected to contain at least this preferred minimum water as a result of the preparation process. One skilled in the art will readily understand, from the above discussion, how to adjust the concentration of the permanganate solution to produce an impregnated support containing an appropriate amount of both permanganate and water.

The permanganate-impregnated support must be wetted with a strongly acidic or alkaline solution to activate it for detection of ethanol vapor. Where an acidic solution is used to activate the impregnated support, the color changes from pink to colorless in the presence of readily oxidizable organic vapors. Suitable acids for preparing the activating solution include strong mineral acid such as sulfuric, nitric, perchloric and other common acids. Where an alkaline solution is used to activate the support, the color changes from pink first to dark green in the presence of readily oxidizable organic vapors, and then to brown in the presence of additional, readily oxidizable organic vapors. Because the color changes more rapidly, and the color change is more distinct, use of the alkaline solution is preferred. Solutions of sodium hydroxide are more preferred as the alkaline activating solution, but solutions of alkali-metal and alkaline-earth hydroxides such as potassium hydroxide, barium hydroxide, cesium hydroxide and lithium hydroxide are contemplated as being within the scope of the present invention. The concentration of the acidic or alkaline activating solution may vary over a wide range. Where activating solutions having concentrations below about 2 molar are used, the color change is slow, and therefore such concentrations are less preferred. A more preferred concentration for the acidic or alkaline activating solution is from about 10% to about 50%, more preferably from about 15% to about 25%, by weight, of acid or alkali, based on the total weight of acid or alkali plus solvent.

The volume of activating solution used to wet the impregnated support is preferably sufficient to uniformly wet the support particles without having free, unabsorbed liquid present. Thus the volume may vary within a relatively wide range without detriment to the reaction. A preferred volume-weight ratio of activating solution to impregnated support is from about 0.1:1 to about 1:1, based on the volume of activating solution, in milliliters, to the weight of impregnated support, in grams. A means for determining the volume of the sample is preferably provided; this may be a gas-flow meter, an integrating gas-flow meter that indicates the total volume directly, or preferably a flexible, impervious, inelastic vessel of known volume which may be inflated by the gas sample, such as a gas-sampling bag.

The method for semi-quantitative estimation of alcohol content in alveolar breath or other gas involves passing a known amount of the gas through the wetted, permanganate-impregnated support and observing the amount of support in which the color change occurs. The permanganate-impregnated support is preferably contained, for this method, in a transparent or translucent vessel through which the gas may pass from an inlet opening to an outlet opening, as for example a tube, so that the color change may easily be observed. The permanganate-impregnated support may be wetted with the alkaline or acidic solution prior to placing it in the vessel, but preferably the solution and the support are kept separate until immediately prior to introducing the sample.

In a preferred embodiment, the dry, permanganate-impregnated support is separated from the acidic or alkaline solution by a plug or screen of glass wool, stainless steel, copper or other inert material. Such an embodiment is shown in FIG. 1. The gas is introduced into the tube from the end containing the solution, so that the gas flow itself forces the solution through the barrier plug or screen and into contact with the permanganate-impregnated support. Thus the gas flow, e.g., breath blown through the tube, is the means for allowing the solution to contact the support. In another preferred embodiment, a check valve is placed in the path of the gas flow, to prevent any of the acidic or alkaline solution from being drawn back toward the inlet opening. This is particularly useful when the gas is human breath blown into the vessel by a human test subject.

Figure 2:
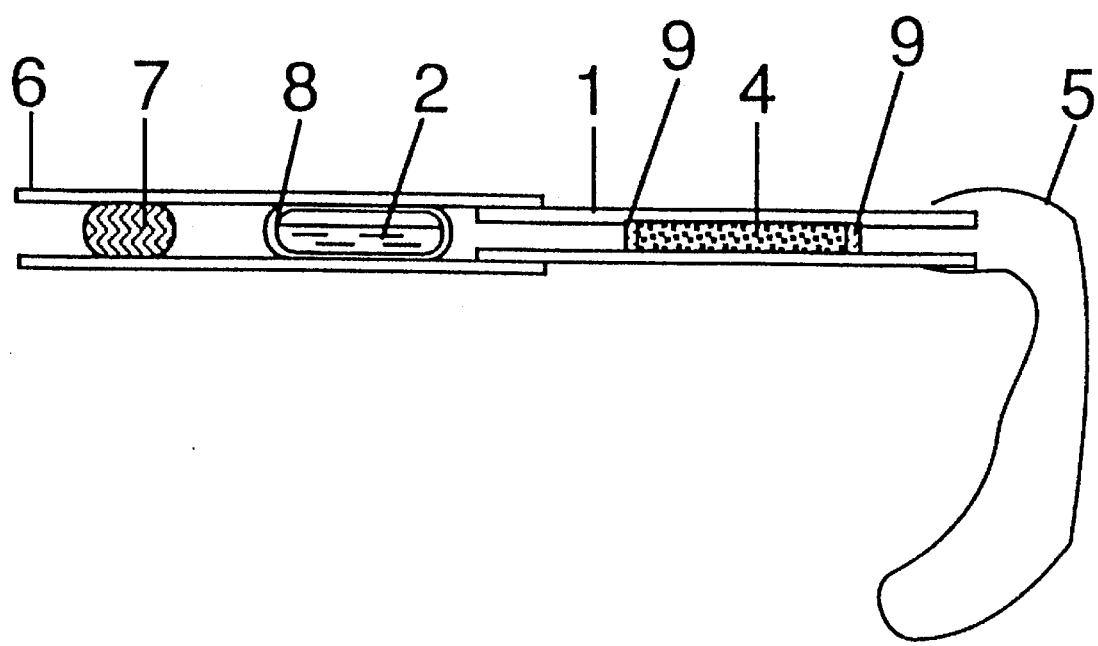
FIG. 2 shows another embodiment of the device of the present invention for estimating readily oxidizable organic vapors in gas samples, and particularly ethanol in breath samples. The permanganate-impregnated support (4) is disposed within the tube (1) and held in place with inert metal screens (9). One end of the tube is connected to the gas-sampling vessel (5), and the other end is connected to a flexible plastic tube (6) within which are disposed a porous closure (7) of glass wool, cotton wool or the like and a frangible ampoule (8) containing the activating reagent (2), the vial also acting as a seal in the plastic tube, protecting the impregnated support from contamination prior to use.

In yet another preferred embodiment, the acidic or alkaline solution is separated from the permanganate-impregnated support by a frangible barrier which may be broken to release the solution immediately prior to introducing the gas sample. Thus the solution may be contained during storage, and the dry, permanganate-impregnated support is not subjected to conditions under which it would rapidly deteriorate. Such an embodiment is shown in FIG. 2. The frangible barrier in this embodiment is a glass ampoule which retains the acidic or basic solution. The ampoule is disposed within the vessel on the side of the barrier plug or screen toward the inlet opening, or preferably within a second vessel having inlet and outlet openings, the outlet opening of the second vessel being connected to the inlet opening of the vessel in which the impregnated support is disposed. The impregnated support is disposed on the side of the barrier plug or screen toward the outlet opening of the vessel containing the support, and the impregnated support may further be retained in place by an additional barrier plug or screen disposed within the vessel nearer to the outlet opening than the support. As noted above, any of the barrier plugs or screens may be made of an inert material such as glass wool, stainless-steel screen or copper screen. The vessel itself, or the preferred second vessel, is made of a transparent or translucent, flexible, non-frangible material, as for example Teflon material. Prior to use, the frangible barrier, e.g. the ampoule, is broken or crushed to release the solution.

The following examples are intended to illustrate the present invention and not to limit it except as it is limited in the claims. All ratios and percentages herein are by weight unless otherwise specified, and all reagents are of good commercial quality unless otherwise specified.

EXAMPLE 1

This example illustrates preparation of the permanganate-impregnated support of the present invention using a molecular sieve support.

A permanganate solution was prepared by dissolving 0.5 g potassium permanganate in 30 ml of distilled water. A 15 g portion of molecular sieve ( Supelco Inc. 13×, 425–600μm) was weighed into a 125-ml glass container, and 4 ml of the permanganate solution was added to the molecular sieve dropwise, with agitation, over a period of five minutes. The resulting, permanganate-impregnated support had a uniform pink color, and contained approximately 3.5 mg potassium permanganate per gram of impregnated support. The impregnated support was stored under nitrogen in a brown-glass container at room temperature.

EXAMPLE 2

This example illustrates preparation of the permanganate-impregnated support of the present invention using a silica gel support. A 15 g portion of silica gel (Merck, 60A, grade 60, 38–63 gm) was weighed into a 125-ml glass container, and 4 ml of permanganate solution prepared according to Example 1 was added to the silica gel dropwise, with agitation, over a period of five minutes. The resulting, permanganate-impregnated support had a uniform pink color, and contained approximately 3.5 mg potassium permanganate per gram of impregnated support.

EXAMPLE 3

This example illustrates the method of the present invention using the permanganate-impregnated support of Example 1, activated with a strongly alkaline solution, to show the change in color observed when the activated support is exposed to a simulated breath sample containing a known amount of ethanol.

Approximately 280 mg of permanganate-impregnated support, prepared according to the procedure of Example 1 but containing 6.6 mg potassium permanganate per gram of the 425–600-μm molecular sieve support, was packed into a 13-cm length of 4-mm inside-diameter (ID) glass tubing plugged at one end with glass wool, to form a column of impregnated support approximately 2.7 cm long in the center of the tube. Another glass wool plug was inserted to hold the packed, impregnated support. Approximately 0.1 ml of a 20% aqueous sodium hydroxide solution was injected into the tube with a micro-syringe. The sodium hydroxide solution formed a column of liquid in the tube separated about 2 cm from the column of solid indicator. A gas sample bag (Safetrip, Oldcastle, Ontario, Canada, 210–220 ml when fully inflated) was connected to the end of the glass tube closest to the solid indicator. The apparatus containing these reagents is shown in FIG. 1.

The end of the glass tube nearest the sodium hydroxide solution was connected to a device for producing a gas sample containing a known concentration of ethanol (a Toxitest II Alcohol Breath Simulator made by CMI Inc., Owensboro, Ky. was used). Nitrogen containing an amount of alcohol vapor which corresponds to a 0.10% blood alcohol content (BAC) at 34° C. (0.10 g/100 ml blood) from the simulator was passed through the tube at a rate sufficient to inflate the gas sample bag over a period of 30 seconds. The nitrogen flow wetted the alkaline solution and the pink color progressively changed to dark green along the length of the impregnated-support column as the gas sample bag inflated. After the gas sample bag was fully inflated, the tube was disconnected from the apparatus. The length of the green-colored portion of the activated support was measured and found to be approximately 2.0 cm.

EXAMPLE 4

This example illustrates the use of the method of the present invention for estimating the content of ethanol in breath samples.

A breath sample of 200–220 ml was blown through the tube containing the impregnated support as described in Example 3, the test subject blowing into the end of the tube nearest the sodium hydroxide solution. The solid indicator was wetted with the alkaline solution and changed color from pink to dark green instantly when alcohol was present in the breath sample. The alcohol content in the breath was estimated by comparing the length of the color changed portion of the indicator to similarly measured lengths of tubes from breath samples of known alcohol content over the range of interest.

A test subject consumed four 340-ml bottles of Coors Light® beer over a period of one and half hours. Fifteen minutes after he finished his last drink, his breath sample was blown into the apparatus. When the gas sample bag was fully inflated, the portion of the impregnated support which had changed to a green color portion was measured as approximately 0.5 cm; based on the length of the impregnated support which changed color in response to a sample corresponding to 0.10% BAC, as measured above in Example 3, his BAC was estimated to be approximately 0.03%.

EXAMPLE 5

This example illustrates correlation of results obtained using the method of the present invention with those obtained using standard methods for determining or estimating breath alcohol content.

For the correlations, two different alcohol testing instruments were used: the BREATHALYZER® Model 900A instrument (manufactured by Smith & Wesson, Springfield, Mass.) which gives quantitative analysis of alcohol content in breath, and the Alcotest® 7410 Breath Alcohol Monitor (Draegerwerk, Lubeck, FRG.) which shows test results of "Pass", "Alert" and "Fail" corresponding to BAC levels of approximately below 0.05%, 0.05–0.10% and above 0.10%, respectively.

The tube packed with impregnated support, as described in Example 3, contained approximately 340 mg of the 425–600-μm molecular sieve of Example 1, impregnated with approximately 4 mg potassium permanganate per gram of support, packed in a 7.5-cm length of 5-mm ID glass tubing and retained by two stainless-steel screens. To one end of the tubing a 200 ml gas sample bag (210–220 ml when fully inflated) was connected. The other end was connected to thin-wall polypropene tubing (7 cm×7 mm ID) into which was placed an onionskin glass capsule (2.5 cm×6.5 mm outside diameter, from Franklin Inc., Franklinville, N.J.) containing 0.14 ml of 20% aqueous sodium hydroxide solution. The open end of the polypropylene tubing was plugged with a cotton ball. The device is shown in FIG. 2.

Forty-one human test subjects were initially tested to determine if their breath contained alcohol. All tests were negative by all three methods employed, as described below. The test subjects consumed different amounts of different types of alcoholic beverages. Breath alcohol tests were administered at least 15 minutes after each subject's last drink, and each subject was tested using all three methods at approximately the same time. Test results were recorded and compared; these semi-quantitative results indicated that the semi-quantitative analysis results from the alcohol testing tube were in agreement with the results from the two breath alcohol analysis instruments.

From the above tests, the following typical results were obtained:

For Test Subject No. 1 the BREATHALYZER Model 900A produced a result of 0.119% BAC, the Alcotest 7410 produced a "Fail" result, and the tube from the method of the present invention produced an indication that the BAC was above 0.1%.

For Test Subject No. 2 the BREATHALYZER Model 900A produced a result of 0.078% BAC, the Alcotest 7410 produced an "Alert" result, and the tube from the method of the present invention produced a result indicating a BAC of between 0.05% and 0.1%.

For Test Subject No. 3 the BREATHALYZER Model 900A produced a result of 0.022% BAC, the Alcotest 7410 produced a "Pass" result, and the tube from the method of the present invention produced a result indicating a BAC reading below 0.05%.

EXAMPLE 6

This example illustrates use of the method and device of the present invention as a quick screening test to indicate whether BAC is above or below 0.1%.

Tubes were prepared according to the procedure described in Example 3, except that two stainless steel screens were used in place of the glass wool, approximately 210 mg of the 425–600-μm molecular sieve of Example 1, impregnated with 6.6 mg potassium permanganate per gram of support, were loaded into each tube, and 0.08 ml of aqueous sodium hydroxide solution was used. A breath sample of 200–220 ml was passed through each tube, which caused the sodium hydroxide solution to wet the impregnated support homogeneously, and the activated support to change color. A column that had changed color only partially indicated a BAC below 0.1%, and the BAC was proportional to the amount of activated support that had changed color. A BAC above 0.2% produced a tube in which the pink color had been entirely replaced, with a brown color occurring nearer the gas inlet, and a dark green color occurring in the remainder of the support.

A test subject consumed an alcoholic beverage (Coors Light beer) at a rate of two 340-ml bottles per half hour. The method of the present invention was used to determine the approximate BAC of the test subject prior to any alcoholic-beverage consumption, after drinking two bottles and waiting 15 minutes, after drinking two more bottles (a total of four) and waiting 15 minutes, and after drinking two more bottles (a total of six) and waiting 15 minutes. The first two tests indicated that the subject's BAC was below the detection limit (no green color was observed). The third test, after four bottles had been consumed, indicated his BAC was below 0.05% (one quarter of the column tuned green). The fourth test, after consumption of six bottles, showed a BAC of greater than 0.1% (the entire column turned green).

EXAMPLE 7

This example illustrates the stability of the impregnated, dry support under storage conditions.

The 425–600-μm molecular sieve of Example 1, impregnated with 4 mg potassium permanganate per gram of support, was stored under nitrogen atmosphere in a sealed brown-glass container at room temperature, and the solid indicator was examined once a month. No color fading was observed after six months. After six months of storage, four tubes were prepared using a method similar to that described in Example 6, except approximately 330 mg of the impregnated support was packed into in each tube. Approximately 0.1 g dry, unimpregnated molecular sieve (13×, 425–600 μm) was placed in the tube at each end of the impregnated support. 0.12 ml of 20% aqueous sodium hydroxide solution was introduced into one end of each tube. A Toxitest II apparatus, as described above, using a standard ethanol solution (Guth Lab., Harrisburg, Pa.) generated a known-ethanol-concentration stream of nitrogen, and this stream was used to simulate the breath of test subjects as described in Example 6. The activated support in each of the four tubes showed a normal color change from pink to green, demonstrating that the dry, impregnated support is stable at least for six months under recommended storage conditions.

EXAMPLE 8

This example illustrates the method of the present invention using a strongly acidic activating solution.

Approximately 0.22 gram of freshly prepared permanganate-impregnated, 425–600-μm molecular sieve bearing 0.7 mg potassium permanganate per gram of support was packed into 4-mm-ID glass tubing and retained with two stainless steel screens as plugs. Approximately 0.08 ml of 50% aqueous sulfuric add was introduced into the tubing, the tubing was connected to a Toxitest II apparatus as described above, and air containing a known concentration of ethanol was blown through the tubing. The acidic solution wetted the impregnated support. The color of the impregnated support was observed periodically; no color change was detected after approximately 30 seconds, at which time approximately 400 ml of ethanol-containing air had been forced through the tubing, but after six minutes, when approximately 2400 ml of ethanol-containing air had been forced through the tubing, approximately 0.2 cm of the indicator turned light brown. As may be seen from this, the color change for impregnated support activated with strongly acidic solution clearly observable, although it is slower and less distinctive than the change with alkaline-activated, impregnated support.

What is claimed is:

1. An activated, impregnated support suitable for the colorimetric estimation of readily oxidizable organic vapors in gases by formation of green manganate which comprises a solid particulate support having adsorbed thereon a permanganate salt, the support being wetted with an alkaline solution, the alkalinity of said solution being sufficient, upon contact of said permanganate salt with said solution and said organic vapors, to cause oxidation of ethanol that may be present in said organic vapors, and reduction of said permanganate to green manganate.

2. The activated support of claim 1 wherein the alkaline solution is at least 2 molar.

3. The activated support of claim 1 wherein the alkaline solution is an aqueous solution of from about 10% to about 50%, by weight, of sodium hydroxide.

4. The activated support of claim 1 wherein the alkaline solution is an aqueous solution of from about 15% to about 25%, by weight, of sodium hydroxide.

5. An activated, impregnated support suitable for the colorimetric estimation of readily oxidizable organic vapors in gases by formation of green manganate which comprises a solid particulate support having adsorbed thereon a permanganate salt, the support being wetted with an alkaline solution containing at least about 10% by weight of an alkali metal hydroxide or alkaline earth metal hydroxide, the alkalinity of said solution being sufficient that upon contact of said permanganate salt with said solution and said organic vapors, any ethanol that may be present in said organic vapors will be oxidized and reduced said permanganate to green manganate.

6. An apparatus for colorimetric estimation of the concentration of readily oxidizable organic vapors in gases which comprises:

a transparent or translucent vessel having an inlet opening and an outlet opening;

disposed within the vessel, an inert, porous, solid support impregnated with a permanganate salt;

further disposed within the vessel, an alkaline solution having sufficient alkalinity to cause the oxidation of ethanol that may be contained in said organic vapors, and reduction of permanganate to green manganate, upon contact of said permanganate salt with said solution and with said organic vapors; and means by which said permanganate salt may be contacted with said solution.

7. An apparatus as set forth in claim 6 wherein the vessel comprises a flexible, non-frangible tube, said alkaline solution is disposed within the vessel nearer than said support to said inlet opening, and the solution is separated from the support by an impervious, frangible barrier disposed within the tube in such a manner that flexing the tube causes the barrier to break and the solution to be released and wet the support.

8. The apparatus of claim 7 wherein the frangible barrier is a glass barrier which entirely surrounds the solution.

9. The apparatus of claim 8 wherein the glass barrier is a glass ampoule.

10. The apparatus of claim 6 wherein the vessel is cylindrical, and the inlet and outlet openings are disposed at either end of the cylindrical vessel.

11. The apparatus of claim 10 wherein the inlet opening is sized such that it is readily sealable by the lips of an adult human being.

12. The apparatus of claim 11 wherein the outlet opening of the vessel is connected to a means for determining the volume of gas which passes through the vessel.

13. The apparatus of claim 12 wherein the means for determining the volume of gas is a gas-sampling bag.

14. An apparatus as set forth in claim 6 wherein said alkaline solution is disposed within said vessel nearer than said support to said inlet opening and separated from said support by a barrier disposed within the vessel, the barrier being sufficiently porous to allow the solution to be forced, under pressure introduced at the inlet opening, through the barrier to contact and wet the support and contact the permanganate salt on the support, but not sufficiently porous to allow the solution to flow through the barrier by capillary action or gravity.

15. The apparatus of claim 14 wherein the barrier is glass fibers.

16. The apparatus of claim 14 wherein the barrier is fritted ceramic.

17. The apparatus of claim 14 wherein the barrier is a stainless-steel screen.

18. The apparatus of claim 14 wherein the barrier is a copper screen.

19. An apparatus for colorimetric estimation of the concentration of readily oxidizable organic vapors in gases which comprises:

a transparent or translucent vessel having an inlet opening and an outlet opening;

disposed within the vessel, an inert, porous, solid support impregnated with a permanganate salt;

further disposed within the vessel, an alkaline solution containing at least about 10% by weight of an alkali metal or alkaline earth metal hydroxide the alkalinity of said solution being sufficient that upon contact of said permanganate salt with said solution and said organic vapors, any ethanol that may be present in said organic vapors will be oxidized and reduce said permanganate to green manganate; and means by which said permanganate salt may be contacted with said solution.

20. A process for estimating the concentration of readily oxidizable organic vapors in a gas sample of known volume which comprises contacting the gas sample with an inert, porous, solid support impregnated with a permanganate salt and activated by wetting with an alkaline solution of sufficient alkalinity so that permanganate salt is reduced to green manganate salt upon contact of said permanganate salt with said solution and said readily oxidizable organic vapors, observing the volume of support in which a color change occurs, and estimating the amount of readily oxidizable organic vapors in the sample by comparison to the volume of activated, permanganate-impregnated support which changes color in response to a gas sample of similar volume containing a known concentration of readily oxidizable organic vapors containing ethanol.

21. The process of claim 20 wherein the volume of the solution is in a ratio to the weight of the support of from about 0.1:1 to about 1:1.

22. The process of claim 20 wherein the alkaline solution is a solution of from about 10% to about 50%, by weight, of sodium hydroxide in water.

23. The process of claim 22 wherein the alkaline solution is a solution of from about 15% to about 25%, by weight, of sodium hydroxide in water.

24. The process of claim 20 wherein the gas sample is a sample of human breath, the readily oxidizable organic vapor is ethanol, and the breath sample is blown through the support by a human test subject.

25. The process of claim 24 wherein the alkaline solution and the support are initially disposed at separate locations within an tube, and the solution is caused to wet the support by the breath sample being blown through the tube.

26. The process of claim 25 wherein the alkaline solution is contained in a frangible ampoule, and the ampoule is broken immediately before the breath sample is blown through the tube.

27. The process of claim 20 wherein the support is molecular sieves.

28. The process of claim 27 wherein the support contains from about 0.7 to about 14 milligrams potassium permanganate per gram of support.

29. The process of claim 27 wherein the support contains from about 3 to about 7 milligrams of potassium permanganate per gram of support, the gas sample is a sample of human breath, the readily oxidizable organic vapor is ethanol, the breath sample is blown through the support by a human test subject, and the volume of the sample is from about 200 to about 250 milliliters.

* * * * *